(12) United States Patent
Elrod et al.

(10) Patent No.: US 7,976,780 B2
(45) Date of Patent: Jul. 12, 2011

(54) METHOD AND APPARATUS FOR MEASURING ISOTOPIC CHARACTERISTICS

(75) Inventors: Louis W. Elrod, Houston, TX (US); Christopher M. Jones, Missouri City, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 1035 days.

(21) Appl. No.: 11/203,796

(22) Filed: Aug. 15, 2005

(65) Prior Publication Data
US 2007/0178011 A1  Aug. 2, 2007

(51) Int. Cl.
G01N 27/00 (2006.01)
G01N 30/02 (2006.01)
G01N 31/12 (2006.01)
G01N 35/00 (2006.01)
G01N 23/00 (2006.01)
G01N 21/72 (2006.01)
G01N 24/00 (2006.01)
G01N 1/22 (2006.01)

(52) U.S. Cl. ........ 422/78; 422/54; 422/62; 422/70; 422/80; 422/89; 422/94; 436/43; 436/57; 436/155; 436/161; 436/173; 436/181; 73/23.35; 73/23.37; 73/61.52

(58) Field of Classification Search .......... 422/54, 422/62, 70, 80, 89, 94; 436/57, 155, 161, 436/173; 356/315, 318, 319; 73/23.35, 23.37, 73/61.52
See application file for complete search history.

(56) References Cited

U.S. PATENT DOCUMENTS

| 5,012,052 | A |   | 4/1991 | Hayes |
| 5,147,611 | A | * | 9/1992 | Stout et al. .............. 422/78 |
| 5,432,344 | A |   | 7/1995 | Brand |
| 5,661,038 | A |   | 8/1997 | Brenna |
| 5,766,954 | A |   | 6/1998 | Freedman |
| 5,783,741 | A |   | 7/1998 | Ellis |
| 2003/0160164 | A1 |   | 8/2003 | Jones |

FOREIGN PATENT DOCUMENTS
GB  2 304 189  3/1997

OTHER PUBLICATIONS

Sharp et al., Geochimica Et Cosmochimica Acta, vol. 60, No. 15, pp. 2909-2916, 1996.*
Wiechert et al., Chemical Geology, 182, 2002, pp. 179-194.*
International Search Report, Jan. 24, 2007.
Price, J.G.W. "Thermal Extraction Chromatography—New Technique for Rapid Wellbore Evaluation," The Journal of Canadian Petroleum, Sep.-Oct. 1985, Montreal (pp. 63-68).

* cited by examiner

*Primary Examiner* — Jill Warden
*Assistant Examiner* — Dean Kwak
(74) *Attorney, Agent, or Firm* — Conley Rose, P.C.

(57) ABSTRACT

Methods and apparatus are provided to measure isotopic characteristics of a number of sample types. Embodiments of the invention combine novel and existing components to produce more accurate isotopic information. Further, embodiments of the invention allow for isotopic readings to be taken and analyzed outside of a laboratory. An example of such an embodiment is an apparatus comprising a combustion furnace; a reactant tube passing through the combustion furnace; an injector coupled to one, or a combination of, the combustion furnace, and reactant tube, to introduce a sample; a laser isotopic measurement device coupled to the reactant tube on the exit end; and a processor electrically coupled to one, or a combination of, the injector, the combustion furnace, the reactant tube, and the isotopic measurement device, in which a carrier gas transports the sample through the apparatus.

10 Claims, 9 Drawing Sheets

METHOD AND APPARATUS FOR MEASURING ISOTOPIC CHARACTERISTICS

FIELD OF TECHNOLOGY

Embodiments of the present invention relate to the field of stable isotopic analysis. Specifically, embodiments relate to sample measurement of whole isotope numbers and isotopic profiles.

BACKGROUND OF INVENTION

In the oil exploration industry, it is necessary to take samples during the process of drilling oil. Sampling decisions include choosing the timing intervals in which to sample, the physical location to take the sample and at what quality level the sample is to be collected. Isotope values of whole oils are useful to compare oils to one another for correlation, but are not available at the wellsite. Currently, isotope values for oil can only be determined in the lab due to bulky, sensitive instrumentation not suitable for use onsite. Thermal extraction is used to determine many types of information from oil, but is not currently used for isotopic analysis.

Isotopic analysis is also used to determine the origin or content of products. Governmental regulatory authorities may use isotopic analysis to determine whether products, such as honey or juice, have been cut with cheaper ingredients than claimed. Products that have increased value based on their origin, such as wine, are analyzed to trace their origin isotopically. Currently, such tests are done in laboratories, which require sample shipment and long testing times.

Forensic science utilizes limited forms of isotopic analysis to determine the content and origin of illegal drugs and crime scene evidence. The military uses isotopic analysis to study explosive residue, starting materials and soil affected by explosions. Presently, most methods of isotopic analysis are performed in laboratories due to the sensitivity and bulkiness of the equipment needed. The analysis performed is slow and gives only limited isotopic information.

BRIEF DESCRIPTION OF THE DRAWINGS

Embodiments of the invention may be best understood by referring to the following description and accompanying drawings which illustrate such embodiments. The numbering scheme for the Figures included herein are such that the leading number for a given reference number in a Figure is associated with the number of the Figure. Reference numbers are the same for those elements that are the same across different Figures. In the drawings.

DETAILED DESCRIPTION OF THE EMBODIMENTS OF THE PRESENT INVENTION

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The embodiments of the present invention relate to novel methods to obtain whole isotope numbers and isotopic profiles of various samples. When describing the apparatus and methods, the following terms have the following meanings, unless otherwise indicated.

Definitions

As used herein, "combustion furnace" refers to a device in which a reactant tube can be maintained at a temperature required for reaction with a substance as it passes over the heated reactant or catalyst. For example, a copper oxide reactant tube may be held at 550° C. so that an oil sample may be injected into the heated reactant tube and converted to carbon dioxide and water.

As used herein, "injector" refers to a mechanism for introducing a sample into the apparatus for testing. The injector may be a port through which a syringe can inject a sample volume.

As used herein, "sample" refers to a representative portion of a whole. Further, sample may be defined as a small segment or quantity taken as evidence of the quality or character of the entire group or lot. Gove, Philip Babcock, ed. *Webster's Third New International Dictionary*, Springfield, Mass., 1993 p. 2008. Examples of samples used for isotopic analysis may include oil, cuttings, drilling fluid, downhole gases, honey, juice, drugs, parts of cigars, fruits, vegetables, etc.

As used herein, "reactant tube" refers to a structure in which the sample passes that is made up of or contains a substance in which the sample chemically reacts with. For example, a reactant tube may be made up of copper oxide that when heated and when an oil sample is exposed to the reactant tube, carbon dioxide is produced for isotopic analysis.

As used herein, "isotopic measurement device" refers to an analytical unit that is capable of measuring the isotopic characteristics of a sample. Examples of isotopic measurement devices may be mass spectrometers and laser spectrometers.

As used herein, "processor" refers to a unit that subjects data or samples to a particular method, system or technique of preparation, handling, or other treatment designed to effect a particular result. Gove, Philip Babcock, ed. *Webster's Third New International Dictionary*, Springfield, Mass., 1993 p. 1808.

As used herein, "carrier gas" refers to a gas introduced in order to transport a sample for analytical purposes. A carrier gas may be an inert gas that will not react with the sample to be transported or with reactants through which it passes. Examples of common carrier gases may be helium and argon.

As used herein, "memory device" refers to a unit designed to store data, information or parameters. For example, a memory device may store data and the experimental parameters under which the data was obtained.

As used herein, "data output" refers to information produced from some process or experiment. For example, in measuring the isotopic characteristics of a sample, data output may include the isotope number of the sample, the parameters of the experiment, the number of components in a sample, etc.

As used herein, "isotopic laser spectrometer" refers to a spectrometer in which the source is a laser and the instrument is specifically adapted to measure the isotopic characteristics of a sample. For example, the spectrometer may require specific wavelength settings and type of detector.

As used herein, "scrubbed" refers to separating some component from a gas. Gove, Philip Babcock, ed. *Webster's Third New International Dictionary*, Springfield, Mass., 1993 p. 2042. For example, carbon dioxide may be separated from air by chemical or mechanical means.

As used herein, "convert" refers to changing or turning from one state to another; altering in form, substance or quality. Gove, Philip Babcock, ed. *Webster's Third New International Dictionary*, Springfield, Mass., 1993 p. 499. For example, an oil sample may be converted to carbon dioxide and water when reacted with copper oxide at high temperatures.

As used herein, "thermal extraction device" refers to a device in which the process of vaporizing volatile components occurs, whether the sample matrix is solid, semi-solid, or liquid. The volatilization of the sample may be controlled by programming the temperature elevation speed and intervals of elevation.

As used herein, "volatize" refers to a substance vaporizing or becoming gaseous at a given temperature. Bennett, H., ed., *Concise Chemical and Technical Dictionary*, New York, 1986 p. 1204. For example, a sample may volatize from liquid to a gas when heated in a furnace.

As used herein, "separate" refers to isolating one or more components from a mixture. Gove, Philip Babcock, ed. *Webster's Third New International Dictionary*, Springfield, Mass., 1993 p. 2069. For example, a chemical species may be separated from a mixture on the basis of its size or electrical charge.

As used herein, "measuring" refers to ascertaining the quantity, mass, extent or degree of in terms of a standard unit or fixed amount. Gove, Philip Babcock, ed. *Webster's Third New International Dictionary*, Springfield, Mass., 1993 p. 1400. Isotopic characteristics may be measured with the use of an isotopic laser spectrometer, for example.

As used herein, "processing" refers to subjecting to a particular method, system, technique of preparation, handling or other treatment designed to effect a particular result. Gove, Philip Babcock, ed. *Webster's Third New International Dictionary*, Springfield, Mass., 1993 p. 1808. For example, data collected from a measurement instrument may be processed by storing, formatting, categorizing, etc.

As used herein, "heating" refers to raising the temperature of a substance. Gove, Philip Babcock, ed. *Webster's Third New International Dictionary*, Springfield, Mass., 1993 p. 1045. For example, a combustion furnace may be used to raise the temperature of an oil sample before interacting with a reactant.

As used herein, "chemical separation device" refers to an instrument used to separate a mixture of chemical species. For example, liquid and gas chromatograph instruments separate chemical species by characteristics such as molecule size, shape, charge, affinity to different species, etc.

As used herein, "gas chromatograph" refers to a chromatography unit in which the substance to be separated into its components is transported via a gaseous mobile phase through a chromatographic column containing a stationary phase where the chemical components are separated by differential absorption.

As used herein, "liquid chromatograph" refers to a chromatography unit in which the substance to be separated into its components is transported via a liquid mobile phase through a chromatographic column containing the stationary phase where chemical components are separated by differential absorption. A common example of liquid chromatography is high pressure liquid chromatography (HPLC).

As used herein, "ambient air" refers to the surrounding air. In an experiment, air that is untreated may be incorporated into a device or process by simply being present at the location of the experiment.

Figure 1:
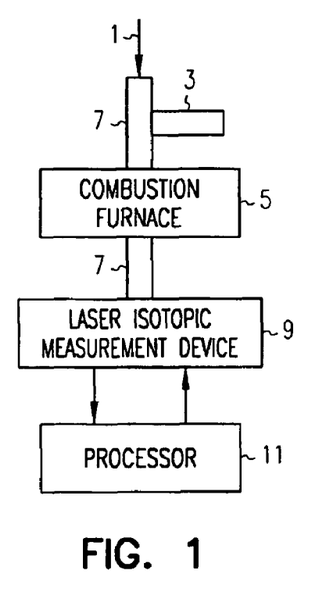
FIG. 1 illustrates a diagram depicting an embodiment of the invention to obtain isotopic characteristics of a sample.

Referring to FIG. 1, an apparatus to measure isotopic characteristics of a sample is provided. An injector (3) is coupled to a combustion furnace (5) to introduce a sample. A reactant tube (7) passes through the combustion furnace (5) and a laser isotopic measurement device (9) is coupled to the reactant tube (7) on the exit end of the reactant tube (7). A processor (11) is electrically coupled to one, or a combination of, the injector (3), the combustion furnace (5), the reactant tube (7), and the laser isotopic measurement device (9). Further, a carrier gas (1) transports the sample through the apparatus.

Figure 2:
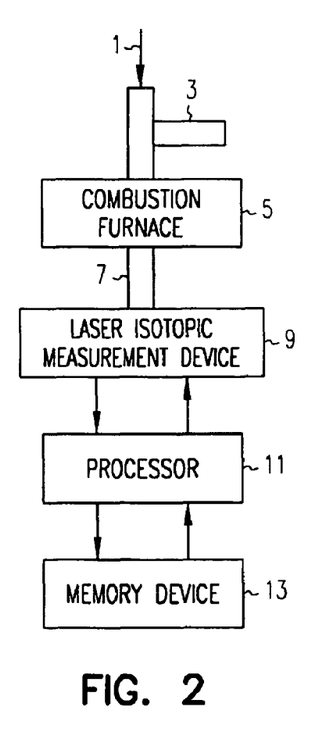
FIG. 2 illustrates a diagram depicting an embodiment of the invention to obtain isotopic characteristics of a sample optionally interfaced with a memory device.

Referring to FIG. 2, an apparatus to measure isotopic characteristics of a sample is provided. An injector (3) is coupled to a combustion furnace (5) to introduce a sample. A reactant tube (7) passes through the combustion furnace (5) and a laser isotopic measurement device (9) is coupled to the reactant tube (7) on the exit end of the reactant tube (7). A processor (11) is electrically coupled to one, or a combination of, the injector (3), the combustion furnace (5), the reactant tube (7), and the laser isotopic measurement device (9). A memory device (13) is electrically coupled to the processor (11) and may be adapted to store one, or a combination of, a combustion furnace temperature, a sample volume, a carrier gas pressure, and a data output. Further, a carrier gas (1) transports the sample through the apparatus.

Figure 3:
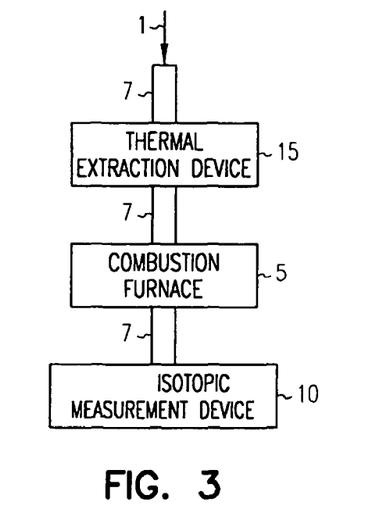
FIG. 3 illustrates a diagram depicting an embodiment of the invention to obtain an isotopic profile of a sample.

Referring to FIG. 3, an apparatus to measure isotopic characteristics of a sample is provided. A thermal extraction device (15), adapted to volatize and separate the sample, is coupled to a reactant tube (7). The reactant tube (7), adapted to convert the sample, passes through the combustion furnace (5), adapted to heat the sample, and an isotopic measurement device (10), adapted for measuring the isotopic characteristics of the sample, is coupled to the exit end of the reactant tube (7). Further, a carrier gas (1) transports the sample through the apparatus.

Figure 4:
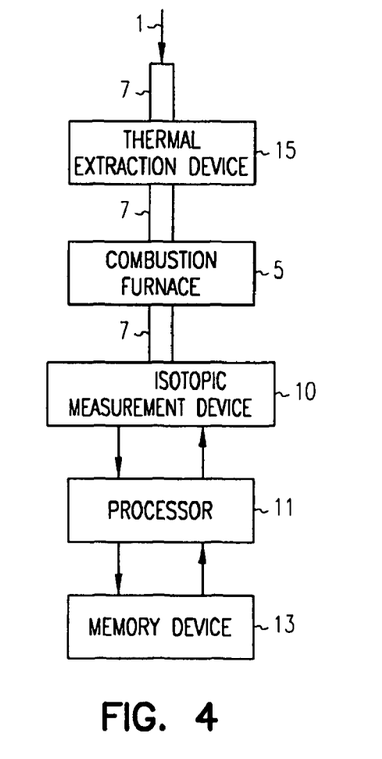
FIG. 4 illustrates a diagram depicting an embodiment of the invention to obtain an isotopic profile of a sample optionally interfaced with a processor and memory device.

Referring to FIG. 4, an apparatus to measure isotopic characteristics of a sample is provided. A thermal extraction device (15), adapted to volatize and separate the sample, is coupled to a reactant tube (7). The reactant tube (7), adapted to convert the sample, is coupled to the combustion furnace (5), adapted to heat the sample, and an isotopic measurement device (10), adapted for measuring the isotopic characteristics of the sample, is coupled to the exit end of the reactant tube (7). A processor (11) is electrically coupled to one, or a combination of, the thermal extraction device (15), the combustion furnace (5), the reactant tube (7), and the isotopic measurement device (9). A memory device (13) is electrically coupled to the processor (11) and may be adapted to store one, or a combination of, a combustion furnace temperature, a sample volume, a carrier gas pressure, and a data output. Further, a carrier gas (1) transports the sample through the apparatus.

Figure 5:
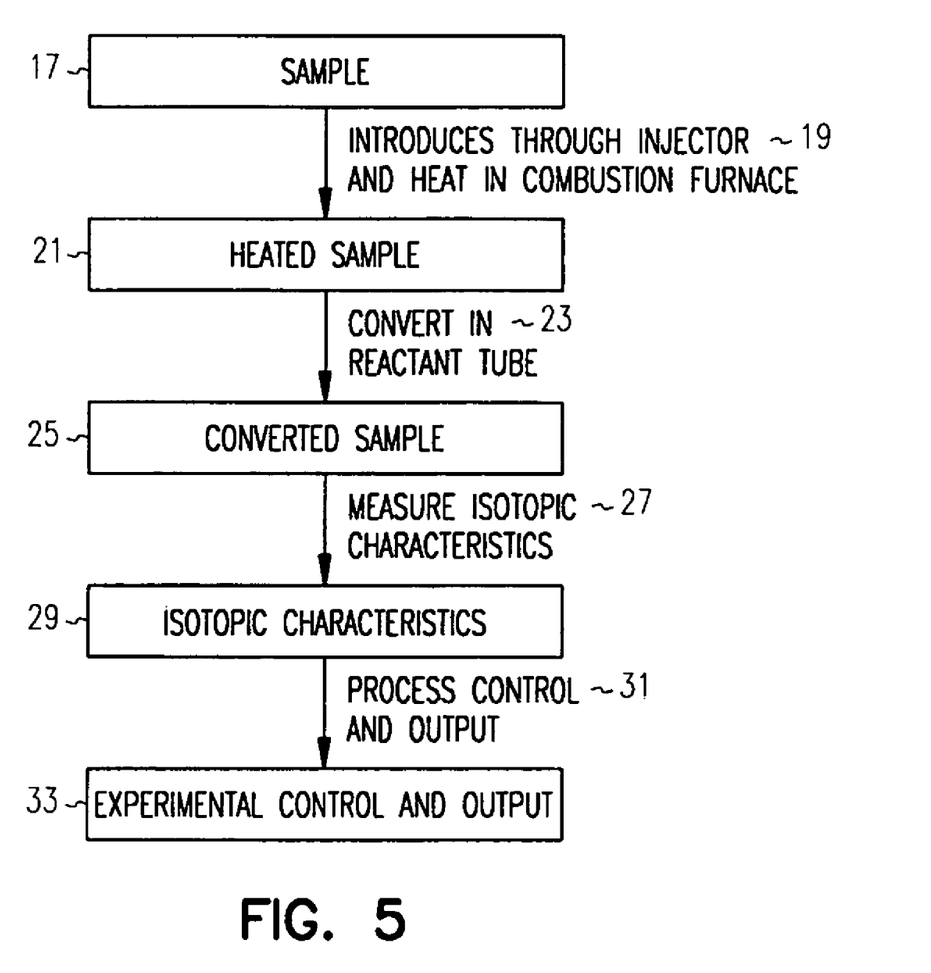
FIG. 5 illustrates a block-flow diagram depicting the obtaining of isotopic characteristics of a sample introduced by an injector.

Referring to FIG. 5, a method to measure isotopic characteristics of a sample is provided. A sample (17) may be introduced (19) through the injector (3) and heated in the combustion furnace (5). The heated sample (21) may be converted (23) in a reactant tube (7) as it passes through the combustion furnace (5). The isotopic characteristics (29) of the converted sample (25) may be measured (27) with a laser isotopic measurement device (9). The control and output of the isotopic characteristics (29) may be processed (31) in order to produce an experimental control and output (33).

Figure 6:
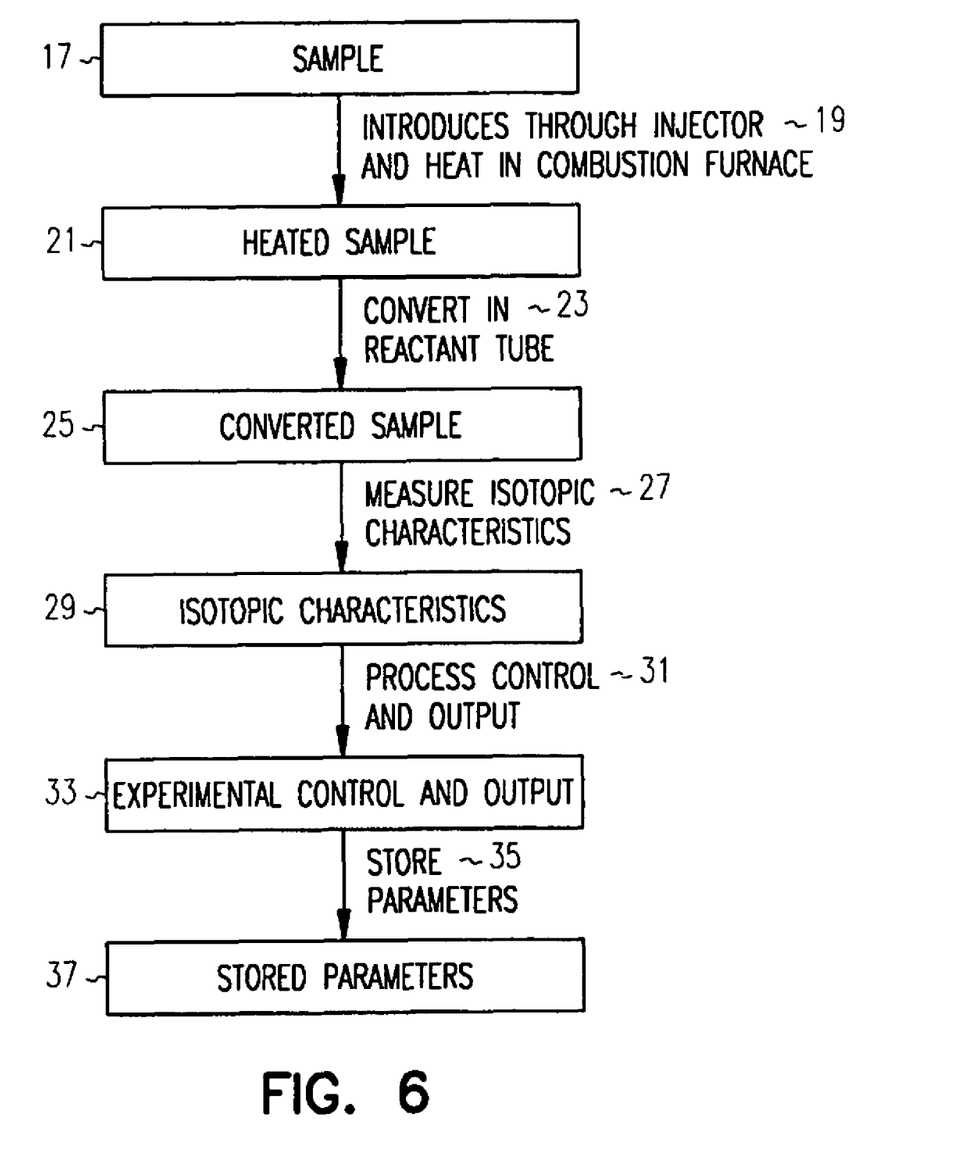
FIG. 6 illustrates a block-flow diagram depicting the obtaining of isotopic characteristics of a sample introduced by an injector including the step of storing the experimental parameters.

Referring to FIG. 6, a method to measure isotopic characteristics of a sample is provided. A sample (17) may be introduced (19) through the injector (3) and heated in the combustion furnace (5). The heated sample (21) may be converted (23) in a reactant tube (7) as it passes through the combustion furnace (5). The isotopic characteristics (29) of the converted sample (25) may be measured (27) with a laser isotopic measurement device (9). The control and output of the isotopic characteristics (29) may be processed (31) in order to produce an experimental control and output (33). The parameters of the experimental control and output (33) may be stored (35) in order to produce stored parameters (37).

Figure 7:
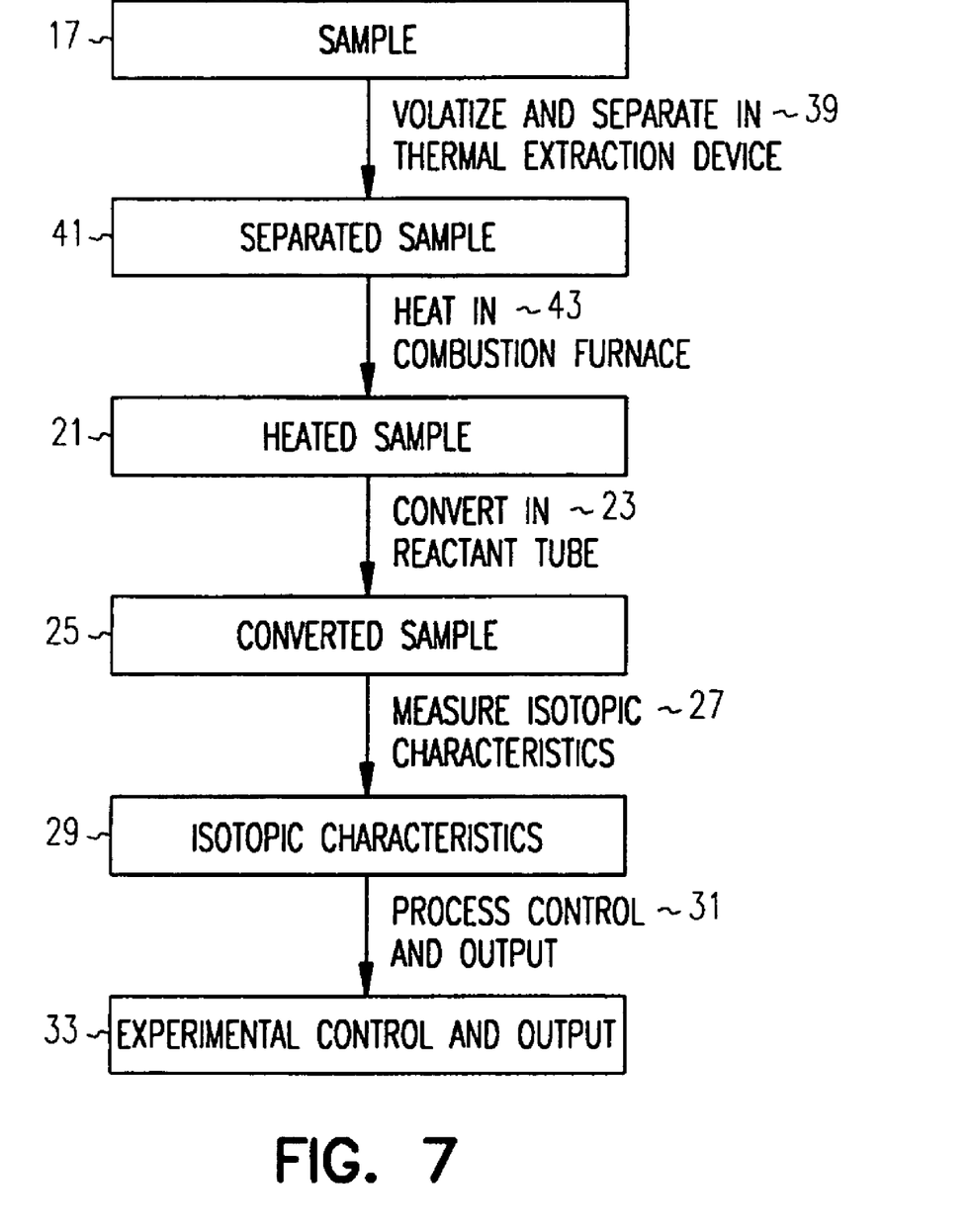
FIG. 7 illustrates a block-flow diagram depicting the obtaining of isotopic characteristics of a sample volatized and separated in a thermal extraction device.

Referring to FIG. 7, a method to measure isotopic characteristics of a sample is provided. A sample (17) may be volatized and separated (39) in the thermal extraction device (15). The separated sample (41) may be heated (43) in the combustion furnace (5). The heated sample (21) may be converted (23) in a reactant tube (7) as it passes through the combustion furnace (5). The isotopic characteristics (29) of the converted sample (25) may be measured (27) with an isotopic measurement device (10). The control and output of the isotopic characteristics (29) may be processed (31) in order to produce an experimental control and output (33).

Figure 8:
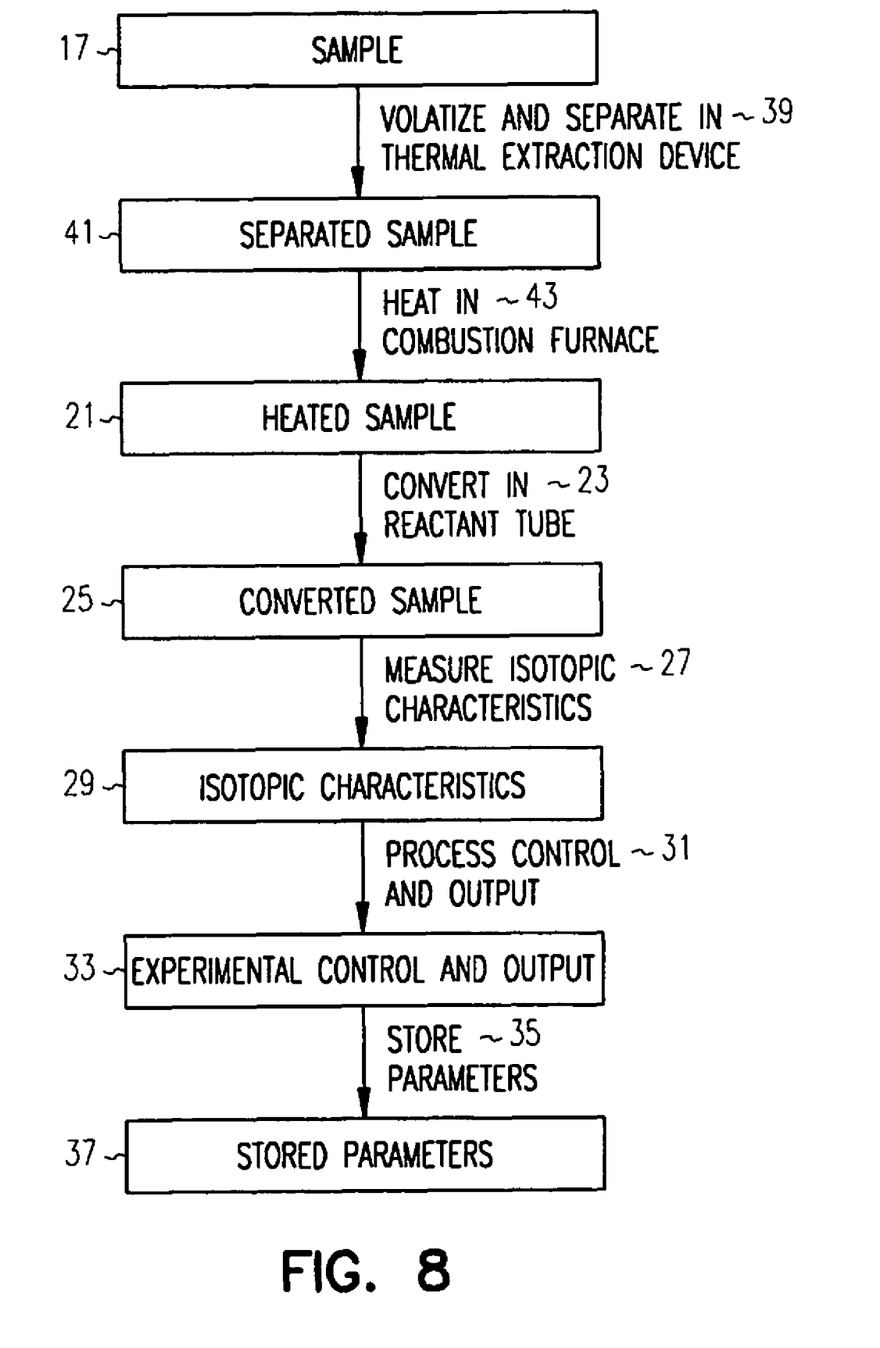
FIG. 8 illustrates a block-flow diagram depicting the obtaining of isotopic characteristics of a sample volatized and separated in a thermal extraction device including the step of storing the experimental parameters.

Referring to FIG. 8, a method to measure isotopic characteristics of a sample is provided. A sample (17) may be volatized and separated (39) in the thermal extraction device (15). The separated sample (41) may be heated (43) in the combustion furnace (5). The heated sample (21) may be converted (23) in a reactant tube (7) as it passes through the combustion furnace (5). The isotopic characteristics (29) of the converted sample (25) may be measured (27) with an isotopic measurement device (10). The control and output of the isotopic characteristics (29) may be processed (31) in order to produce an experimental control and output (33). The parameters of the experimental control and output (33) may be stored (35) in order to produce stored parameters (37).

Figure 9:
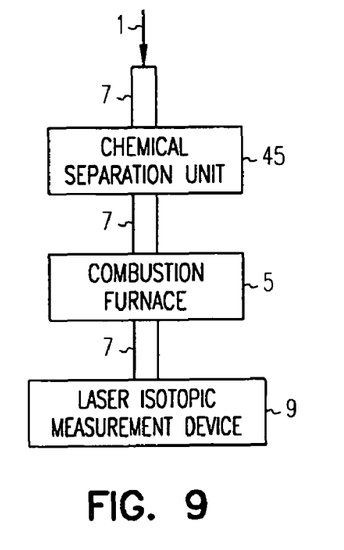
FIG. 9 illustrates a diagram depicting an embodiment of the invention to obtain isotopic characteristics of the chemical fractions of a sample.

Referring to FIG. 9, an apparatus to measure isotopic characteristics of a sample is provided. A chemical separation unit (45), adapted to separate the sample into chemical fractions, is coupled to a combustion furnace (5), adapted to heat the sample. A reactant tube (7), adapted to convert the sample, passes through the combustion furnace (5) and a laser isotopic measurement device (9), adapted for measuring the isotopic characteristics of the sample, is coupled to the exit end of the reactant tube (7). Further, a carrier gas (1) transports the sample through the apparatus.

Figure 10:
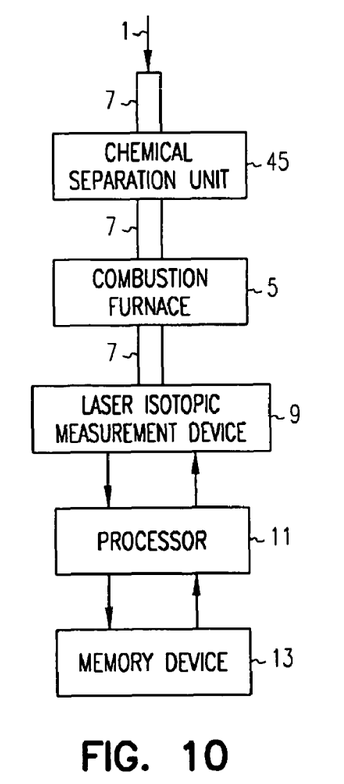
FIG. 10 illustrates a diagram depicting an embodiment of the invention to obtain isotopic characteristics of the chemical fractions of a sample optionally interfaced with a processor and memory device.

Referring to FIG. 10, an apparatus to measure isotopic characteristics of a sample is provided. A chemical separation unit (45), adapted to separate the sample into chemical fractions, is coupled to a combustion furnace (5), adapted to heat the sample. A reactant tube (7), adapted to convert the sample, passes through the combustion furnace (5) and a laser isotopic measurement device (9), adapted for measuring the isotopic characteristics of the sample, is coupled to the exit side of the reactant tube (7). A processor (11) is electrically coupled to one, or a combination of, the chemical separation unit (45), the combustion furnace (5), the reactant tube (7), and the laser isotopic measurement device (9). A memory device (13) is electrically coupled to the processor (11) and may be adapted to store one, or a combination of, a combustion furnace temperature, a sample volume, a carrier gas pressure, and a data output. Further, a carrier gas (1) transports the sample through the apparatus.

Figure 11:
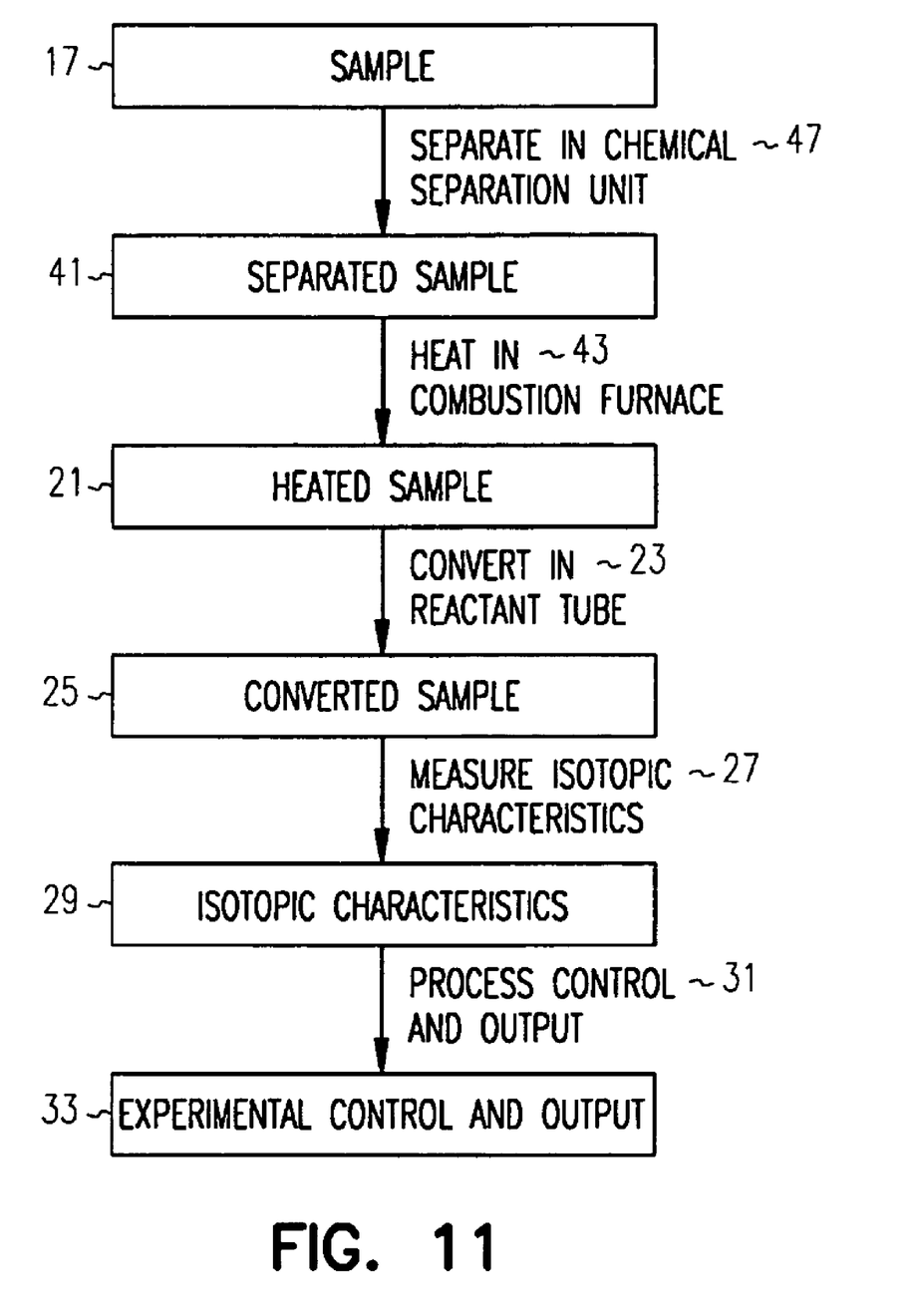
FIG. 11 illustrates a block-flow diagram depicting the obtaining of isotopic characteristics of a sample separated in a chemical separation unit.

Referring to FIG. 11, a method to measure isotopic characteristics of a sample is provided. A sample (17) may be separated (47) in a chemical separation unit (45). The separated sample (41) may be heated (43) in the combustion furnace (5). The heated sample (21) may be converted (23) in a reactant tube (7) as it passes through the combustion furnace (5). The isotopic characteristics (29) of the converted sample (25) may be measured (27) with a laser isotopic measurement device (9). The control and output of the isotopic characteristics (29) may be processed (31) in order to produce an experimental control and output (33).

Figure 12:
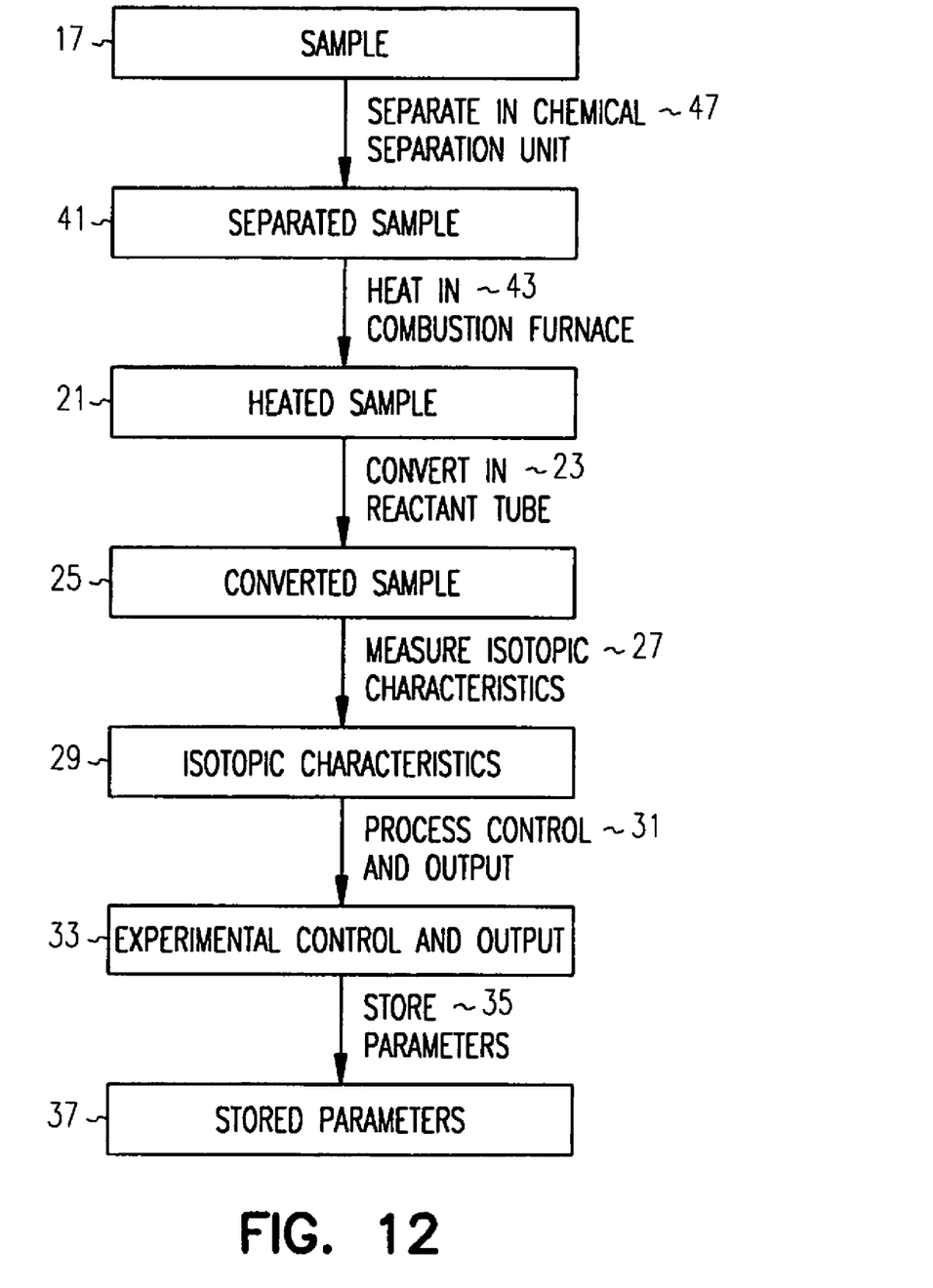
FIG. 12 illustrates a block-flow diagram depicting the obtaining of isotopic characteristics of a sample separated in a chemical separation unit including the step of storing the experimental parameters.

Referring to FIG. 12, a method to measure isotopic characteristics of a sample is provided. A sample (17) may be separated (47) in a chemical separation unit (45). The separated sample (41) may be heated (43) in the combustion furnace (5). The heated sample (21) may be converted (23) in a reactant tube (7) as it passes through the combustion furnace (5). The isotopic characteristics (29) of the converted sample (25) may be measured (27) with a laser isotopic measurement device (9). The control and output of the isotopic characteristics (29) may be processed (31) in order to produce an experimental control and output (33). The parameters of the experimental control and output (33) may be stored (35) in order to produce stored parameters (37).

Referring to FIGS. 1-2 and 5-6, embodiments of the invention are depicted. An apparatus and method to measure isotopic characteristics of a sample is provided. An injector (3) is coupled to a combustion furnace (5) to introduce a sample (17). The injector (3) receives the sample (17) and introduces it into the apparatus to be carried via carrier gas (1) or vacuum to the combustion furnace (5). The injector (3) may be a syringe, for example. The combustion furnace (5) is a device that heats the sample to a specified temperature. The desired temperature depends on the sample and at what temperature the sample converts in the presence of the reactant. The sample (17) may be heated to about 550° to about 950° C., for example.

The sample (17) may be any substance capable of containing isotopic information. For example, the sample may be a carbon source. In the oilfield industry, the sample may be cuttings or drilling fluid, for example. The tracking of isotopic information in the oil industry can lead to a greater understanding of sample quality and geo-steering analysis related to location of drilling, for example. Rapid isotopic characterization of the oil field samples allows for better on-site decision making relative to the timing and location of sample collection.

In forensics, samples may include plastics or fibers. Crime scene evidence may be tracked to its source of origin based on isotopic analysis. Drugs, both legal and illicit, may be suitable samples. Stable isotope measurements of carbon and nitrogen in seized drugs can determine or narrow the geographic site of origin of natural drugs. In addition, carbon and nitrogen isotopes can aid in determining the synthetic process employed and the particular batch or manufacturer of synthetic drugs.

Military or law enforcement may use isotopic analysis when dealing with explosives. A manufactured explosive product will usually have a different isotopic ratio than the starting materials (usually nitrogen ratios) used to produce it. The difference in isotopic ratio can be used to track the factory and process that produced the explosive. Nitrogen isotopic ratios also differ between explosive residues and undetonated explosives due to the lighter isotopes volatizing due to the heat of explosion. Soil samples can be compared to areas where bombs have been dropped and those where bombs may be buried, for example.

Foods and consumables, such as fruit, vegetables, alcohol, juice and cigars, may be used as samples. As an example, the adulteration of honey with corn syrup is a significant problem in its industry, especially with imported honey. The manner in which carbon is incorporated into plants can affect the observed stable isotope content of plant products. Most plants use the $C_3$ photosynthesis process, but sugar cane and corn use the $C_4$ process, which results in differing isotopic values. Since honey is made from $C_3$ plants, direct measurement of the isotopic value of a honey batch can detect adulteration with corn syrup down to about 5-8%.

The mislabeling of orange juice (and other juices) as "fresh squeezed" or "not from concentrate" is another problem within its industry. Water in fruits becomes depleted in $^2H$ and $^{18}O$ relative to the ground water due to the processes encountered in forming the fruit. Isotopic measurement of hydrogen and/or oxygen in juice can distinguish between natural juice and reconstituted juice from ground water sources.

Samples may be solids, liquids or gases. More specifically, the sample may contain any species capable of containing isotopes detectable by an isotopic analysis device. Examples of isotopic species are isotopes of carbon, hydrogen, water, nitrogen, phosphorous, sulfur, and chlorine.

A reactant tube (7) passes through the combustion furnace (5) and is coupled to the isotopic measurement device on its exit end. The reactant tube (7) may be the section of the tube containing reactant inside the combustion furnace (5). The reactant tube (7) may contain a reactant in which the heated sample chemically reacts. The reactant tube (7) may also contain a catalyst in addition to a reactant. The reactant tube (7) may contain copper oxide, for example. Other examples of reactants may include nickel oxide and mixtures with copper oxide. The reactant may be a reagent and may need to be replaceable. The reactant tube (7) itself may be replaceable or solely the reactant contained within. The reactant tube (7) may also be set up to self-replenish so that the reactant tube (7) itself would not have to be physically manipulated. The reactant tube (7) may be constructed in any shape or size so long as it allows sample passage and interaction of the sample with the reactant. An example of a reaction may be the conversion of a heated carbon source to carbon dioxide in the presence of copper oxide. The conversion of a carbon source to carbon dioxide allows for the carbon isotopes to be measured by the isotopic measurement device. Another example may be the conversion of water to hydrogen in order to measure the hydrogen isotopic characteristics. Hydrogen is usually measured as $H_2$ and is obtained from water by reaction with zinc, chromium or manganese, for example. A laser spectrometer might measure the isotope values of hydrogen and oxygen in water directly, which would require no conversion.

An alternative to using the reactant tube (7) for oxidation may be to introduce an oxygen stream with the carrier gas and run it over a platinum catalyst. Further, an air stream could be introduced to provide oxygen, so long as it is scrubbed of carbon dioxide.

A laser isotopic measurement device (9) is coupled to the reactant tube (7) on the exit side of the reactant tube (7). A laser isotopic measurement device (9) may be any analytical tool configured to detect isotopic characteristics of a sample (19). For example, the laser isotopic measurement device (9) may be a laser isotopic spectrometer. A laser spectrometer may be used to detect isotopic characteristics of a sample by adjusting such parameters as the type of laser used as the energy source, the wavelength range scanned and the type of detector used. The laser isotopic measurement device may be configured to detect isotopes of carbon, nitrogen, hydrogen, oxygen, sulfur, phosphorous, chlorine, as examples. An example of an isotopic characteristic detected may be relative isotopic ratios.

A processor (11) is electrically coupled to one, or a combination of, the injector (3), the combustion furnace (5), the reactant tube (7), and the laser isotopic measurement device (9). For example, a processor (11) may be part of a computer used to collect and categorize the data produced from one, or a combination of, the injector (3), the combustion furnace (5), the reactant tube (7) and the isotopic measurement device (9).

A memory device (13) is electrically coupled to the processor (11) and may be adapted to store one, or a combination of, a combustion furnace temperature, a sample volume, a carrier gas pressure, and a data output. For example, the memory device (13) may be a component of a computer used to store such things as experimental settings and data. The memory device (13) may store isotopic data that correlates to certain types or locations of samples. For example, a library of isotopic information may be collected for geographic or regional samples in the oil industry which could allow for comparison of samples in the future.

Further, a carrier gas (1) transports the sample through the apparatus. In order for the sample (17) to flow through the apparatus, a carrier gas (1) must move the volatiles from the introduction point through the reactant tube (7), combustion furnace (5) and to the laser isotopic measurement device (9). Examples of carrier gases (1) include gases inert to the sample (17), such as helium, argon and nitrogen. Another possibility for a carrier gas (1) may be air, scrubbed of carbon dioxide. An alternative to using a carrier gas (1) would be to use a vacuum set up to pull the sample through the apparatus.

Referring to FIGS. 3-4 and 7-8, a further embodiment of the invention is depicted. In place of, or in conjunction with the injector (3), a thermal extraction device (15) may be utilized to introduce the sample (17) through the combustion furnace (5). A thermal extraction device (15) vaporizes volatile components, whether the sample matrix is solid, semi-solid, or liquid. The volatilization of the sample (17) may be controlled by programming the temperature elevation speed and intervals of elevation. In contrast to the rapid entry of sample to the combustion furnace (5) using an injector (3), the thermal extraction device (15) may separate components of the sample by temperature characteristics. The carrier gas (1) or vacuum will pull the extracted components of the sample (17) through the reactant tube (7), combustion furnace (5) and into the isotopic measurement device (10). The isotopic measurement device (10) may be a laser isotopic measurement device (9). More specifically, the isotopic measurement device may be a laser isotopic spectrometer. The result, of which is the determination of mass and isotopic characteristics in profile form. More detailed isotopic information relating to different components of the sample (17) may be determined with the use of a thermal extraction device (15) in the system. The use of an injector (3) alone may be quicker, but will not produce a profile of isotopic information.

Referring to FIGS. 9-12, another embodiment of the invention is shown. In place of, or in conjunction with an injector (3), a chemical separation unit (45) may be utilized. A chemical separation unit (45) is an instrument used to separate a mixture of chemical species. For example, liquid and gas chromatograph instruments separate chemical species by characteristics such as molecule size, shape, charge, affinity to different species, etc. The use of a chemical separation device (45) will separate fractions of a sample (17) before entering the combustion chamber. Isotopic characteristics of the different fractions of the sample (17) can be determined as opposed to a whole isotope number for a bulk sample.

One suitable apparatus for use in carrying out embodiments of the present invention is described, e.g., in U.S. Patent Application Number 20040164237, filed on Mar. 1, 2004, published on Aug. 26, 2004, assigned to Halliburton Energy Services, Inc. The contents of U.S. Patent Application Number 20040164237 are incorporated by reference herein in its entirety. The application relates to a method and apparatus for providing real-time data indicative of the isotopic composition of formation fluids during drilling. The method includes the steps of: providing a reference fluid having a known isotopic composition in a reference cell; capturing a sample of formation; providing at least one laser beam; passing a beam through the reference fluid, measuring the reference-measurement beam before and after it passes through the reference fluid; and passing a beam through the sample, measuring the beam before and after it passes through the sample, and calculating a first isotope concentration from those measurements. The measurements can provide information relating to the carbon isotopic composition of individual compounds in hydrocarbon gas mixtures, with the individual compounds including methane, ethane, propane, iso- or normal butane, or iso- or normal pentane.

In the following claims, the terms "first," "second," and "third," etc. are used merely as labels, and are not intended to impose numerical requirements on their objects.

The invention claimed is:

1. An apparatus for measuring the isotopic characteristics of a sample, the apparatus comprising:
a thermal extraction device adapted to differentiate the sample's components through volatization by progressive temperature elevation of the sample over a period of time, the thermal extraction device being capable of differentiating a solid, a semi-solid, and a liquid sample and producing vapour or gas sample components;
a reactant tube configured to accept the sample components from the output of the thermal extraction device and also adapted to contain and convert the sample components;
a combustion furnace configured such that the reactant tube passes through the combustion furnace, the combustion furnace adapted to combust the differentiated sample components in the reactant tube as they pass through;
a laser isotopic measurement device coupled to the reactant tube on the exit end and adapted to measure the isotopic characteristics of the sample; and
wherein the sample is transportable through the apparatus by a carrier gas.

2. The apparatus of claim 1, further comprising a processor, electrically coupled to one, or a combination of, the thermal extraction device, the combustion furnace, the reactant tube, and the isotopic measurement device, the processor being programmed to produce an experimental control and output.

3. The apparatus of claim 1, further comprising a memory device, adapted to store one, or a combination of, a combustion furnace temperature, a thermal extraction device temperature, a sample volume, a carrier gas pressure, and a data output.

4. The apparatus of claim 1, wherein the reactant tube may be manufactured of a mixture of copper oxide and nickel oxide.

5. The apparatus of claim 1, wherein the reactant tube may contain ambient air, scrubbed of carbon dioxide.

6. The apparatus of claim 1, wherein the isotopic measurement device is an isotopic laser spectrometer.

7. A method to measure isotopic characteristics of a sample, the method comprising the steps of:
differentiating the components of any one of a solid, semi-solid, and liquid sample through volatization by progressively elevating the temperature of the sample over a period of time with a thermal extraction device to produce vapour or gas sample components;
after the components are differentiated, converting the sample in a tube containing a reactant as the sample passes in the tube through a combustion furnace that heats the sample;
after passing through the tube, measuring isotopic characteristics of the combusted sample with a laser isotopic measurement device; and
processing the control and output of the apparatus throughout the process with a computer processor programmed to produce an experimental control and output.

8. The method of claim 7, further comprising storing the parameters of the experimental control and output of the apparatus in a memory device of the computer.

9. The method of claim 7, wherein the combustion furnace heats the sample to about 550° C. to about 950° C.

10. The method of claim 7, wherein the isotopic measurement device is an isotopic laser spectrometer.

* * * * *